United States Patent
Wilhelmi et al.

(10) Patent No.: US 11,883,437 B2
(45) Date of Patent: Jan. 30, 2024

(54) XENOGRAFT SOFT TISSUE IMPLANTS AND METHODS OF MAKING

(71) Applicant: Tutogen Medical GmbH, Neunkirchen am Brand (DE)

(72) Inventors: Arnd Wilhelmi, Forchheim (DE); Silke Schreiner, Erlangen (DE); Jake Michaelson, Gainesville, FL (US); Steven Moore, Apex, NC (US); Jennifer Faleris, Lowell, FL (US); Anne Reinlein, Bamberg (DE)

(73) Assignee: Tutogen Medical GmbH, Neunkirchen am Brand (DE)

( * ) Notice: Subject to any disclaimer, the term of this patent is extended or adjusted under 35 U.S.C. 154(b) by 49 days.

(21) Appl. No.: 17/838,001

(22) Filed: Jun. 10, 2022

(65) Prior Publication Data

US 2022/0296651 A1    Sep. 22, 2022

Related U.S. Application Data

(60) Continuation of application No. 17/013,159, filed on Sep. 4, 2020, now Pat. No. 11,382,933, which is a division of application No. 16/113,951, filed on Aug. 27, 2018, now Pat. No. 10,765,703, which is a division of application No. 13/839,440, filed on Mar. 15, 2013, now Pat. No. 10,076,543, which is a continuation-in-part of application No. PCT/EP2012/000124, filed on Jan. 12, 2012.

(30) Foreign Application Priority Data

Jan. 14, 2011    (DE) .......................... 1020110086048

(51) Int. Cl.
*A61K 35/36*    (2015.01)
*A61L 27/36*    (2006.01)

(52) U.S. Cl.
CPC ............ *A61K 35/36* (2013.01); *A61L 27/362* (2013.01); *A61L 27/3687* (2013.01)

(58) Field of Classification Search
None
See application file for complete search history.

*Primary Examiner* — Russell G Fiebig
(74) *Attorney, Agent, or Firm* — Kilpatrick Townsend & Stockton LLP

(57) ABSTRACT

The present application is directed to the field of implants comprising soft tissue for use in implantation in humans. The soft tissue implants of the present application are preferably obtained from xenograft sources. The present application provides a chemical process that sterilizes, removes antigens from and/or strengthens xenograft implants. The present techniques yield soft tissue implants having superior structural, mechanical, and/or biochemical integrity. The present application is also directed to processes for treating xenograft implants comprising soft tissues such as dermis, and to implants produced by such processes.

18 Claims, 3 Drawing Sheets

XENOGRAFT SOFT TISSUE IMPLANTS AND METHODS OF MAKING

CROSS-REFERENCES TO RELATED APPLICATIONS

This application is a Continuation of U.S. patent application Ser. No. 17/013,159, filed Sep. 4, 2020, which is a Divisional of U.S. patent application Ser. No. 16/113,951, filed Aug. 27, 2018; which is a Divisional of U.S. patent application Ser. No. 13/839,440, filed Mar. 15, 2013; which is a Continuation-in-Part of PCT Application No. PCT/EP2012/000124, filed Jan. 12, 2012 which claims priority from German application DE102011008604.8, filed Jan. 14, 2011, the disclosures of which are incorporated by reference therein.

TECHNICAL FIELD

The present application is directed to the field of biological tissue implants and biological tissue implant processing for transplantation, preferably into humans. The tissue implants are preferably xenograft soft tissue implants, although certain aspects of the present application may apply to other tissues from allograft or xenograft sources. The present application provides a chemical process that sterilizes, removes antigens from and/or strengthens xenograft implants. The present techniques yield soft tissue implants having desired structural and mechanical properties, and/or biochemical integrity. The present application is also directed to processes for treating xenograft implants comprising soft tissues such as dermis, and to implants produced by such processes.

BACKGROUND OF THE INVENTION

Many injuries and ailments throughout the human body are treated through surgical intervention utilizing either biological tissue or synthetic material implants. Among these are conditions including spinal degeneration, sports medicine, podiatric, trauma and general orthopedic injuries or maladies involving bone or hard tissue. Also commonly benefitting from surgical intervention utilizing either biological tissue or synthetic material implants are soft tissue conditions including hernia, urological, gynecological, cardiac, neural, and general abdominal injuries or maladies.

In selecting implants to address these various injuries and maladies, surgeons are often faced with tradeoffs between natural, biological tissue materials and synthetic materials. Biological materials often offer natural healing, incorporation and regenerative capability, but may be lacking in material properties or handling characteristics as compared to synthetics. Surgeons must therefore often choose to accept the lack of regeneration and incorporation potential in using a synthetic material, which is at best inert and at worst inflammatory and prone to infection, in order to find an implant with the physical handling and material properties required for a particular surgical application.

Donated human cadaver (i.e. allograft) tissue has proven to be an efficacious option allowing patients to return to their pre-injury quality of life. However, allograft options are burdened with the challenge of depending on a raw material that has large variability and limited availability. Surgeons have tried to mitigate graft variability by limiting donor criteria (e.g. only accepting grafts from donors<45 years of age); however, such limitations have also exacerbated the availability challenge.

Thus, a goal is to find a sufficient pool of donor tissue, with similar genetic, physical and physiological attributes, that could mitigate or eliminate the above problems. This can be done by utilizing xenograft tissue. With a xenograft tissue source donor genetic makeup can be selected and controlled through breeding and animal management, production can be monitored and controlled to ensure the best health and muscle tone, and donor age can be planned and selected. Such donors would thus have exceptional biomechanical structures available for creating high quality grafts which would be recovered from them at their peak age.

Implants comprising soft tissues may be implanted into a recipient to replace and/or repair existing soft tissues. For example, hereditary defects, disease, and/or trauma may damage soft tissues such that replacement and/or repair is desirable. These implants may be allografts, autografts, or xenografts, and the recipients may be human, mammal, or animal recipients. Implants are frequently used where the recipient is a human patient. Implants comprising soft tissues have been used, including in human patients, to replace heart valves, ligaments, tendons and skin, among other tissues.

It is desirable to treat implants, particularly autografts, allografts, and xenografts, to remove, inactivate or substantially reduce one or more undesirable components or to instill one or more desirable components. For example, implants may be passivated, or treated to remove or inactivate bacteria, viruses, fungi and other pathogens and antigenic constituents.

A desirable treatment process includes one or more of the following features: decellularization, effective removal or inactivation of a wide range of bacterial, viral and fungal pathogens; absence of graft toxicity; retention or improvement of desirable tissue characteristics, such as biomechanical strength or growth-inducing properties; effectiveness across a wide range of operating modifications and/or for a wide variety of tissue types; ability to conclude the process in a final implant tissue container, to ensure sterile packaging and delivery for implantation; ability to apply automated control and monitoring systems and develop an automated and validated process.

A desirable treatment process for xenograft dermal tissue also removes or substantially reduces hair and hair follicles.

BRIEF SUMMARY OF THE INVENTION

The present application is directed to a method of processing a xenograft dermal tissue implant to make it more suitable for transplantation into a human. In one embodiment, the method comprises splitting the dermal tissue, treating the dermal tissue to remove hair, exposing the dermal tissue to a saline solution, exposing the dermal tissue to an oxidizing sterilant; and dehydrating the dermal tissue.

The present application is also directed to a method of processing a xenograft implant where the implant is made from dermal tissue of porcine origin.

The present application is also specifically directed to embodiments utilizing oxidizing sterilants such as peroxides, oxides, hypochlorites, percarboxylic acids, and ozone. Hydrogen peroxide ($H_2O_2$) is preferred.

The present application is also specifically directed to embodiments that expose the dermal tissue to a saline solution in multiple steps. Specifically, one embodiment includes multiple steps of exposing the dermal tissue to a saline solution, with steps of exposing to water in between. This process creates an osmotic gradient.

The present application is also specifically directed to embodiments utilizing sodium sulfide to remove hair from the xenograft dermal tissue.

The present application is also specifically directed to embodiments that further include a rehydration step that occurs after the dehydration step.

The present application is also specifically directed to embodiments that further include punching or stamping grafts of a desired shape from the dermal tissue.

The present application is directed to a method for the preparation of a graft from animal dermis. In one embodiment, the method comprises providing an animal dermis; treating the animal dermis with an aqueous sodium sulfide solution, once or several times; treating the dermis with an aqueous salt solution, once or several times; treating the dermis with an aqueous hydrogen peroxide solution; and dehydrating the dermis. In specific embodiments, the animal dermis is porcine dermis. The present application is also directed to grafts made by the above process.

The present application is also directed to embodiments that further include using an aqueous alkaline, sodium sulfide-containing solution. In specific embodiments, an aqueous solution is used which contains from 0.01 to 10 weight-% of sodium sulfide. In other specific embodiments, an aqueous solution is used which in addition to sodium sulfide contains 0.001 to 0.5 M sodium hydroxide. In further specific embodiments, the dermis is treated in an aqueous sodium sulfide containing solution for 1 to 48 hours, with a solution volume in milliliters that is 5 to 15 times the mass of the dermis in grams.

The present application is also directed to embodiments that treat the dermis two to ten times with an aqueous, 1 to 50 wt-% salt solution, wherein the salt is an alkali metal or alkaline earth metal, such as sodium chloride, potassium chloride, lithium chloride, magnesium chloride or calcium chloride.

The present application is also directed to embodiments that treat the dermis two to five times with an aqueous solution containing 1 to 10 wt-% of hydrogen peroxide, with optional rinsing between each treatment.

The present application is also directed to embodiments that dehydrate the dermis by treating from two to ten times with an organic solvent selected from the group consisting of acetone, methanol, ethanol and isopropyl alcohol.

The present application is also directed to embodiments that include in providing the dermis several steps such as: cleaning the skin of slaughtered pigs with detergent-containing water at a temperature of not more than about 40° C.; removing the skin from the back portion of the pig; removing the bristles from the skin provided above and removal of the subcutaneous tissue and the epidermis from the dermis using a splitting machine.

The present application is also directed to a method of surgery comprising implantation of a graft prepared by the methods above in hernia surgery, for the treatment of hernia or abdominal repair.

These and other advantages and novel features of the present application, as well as details of illustrated embodiments thereof will be more fully understood from the following description of the drawings.

BRIEF DESCRIPTION OF THE DRAWINGS

FIG. 2A shows H&E stained tissue with 50× magnification and frozen cryostat sectioning. FIG. 2B shows Alcian Blue stained tissue with 100× magnification and frozen cryostat sectioning.

Figure 1:
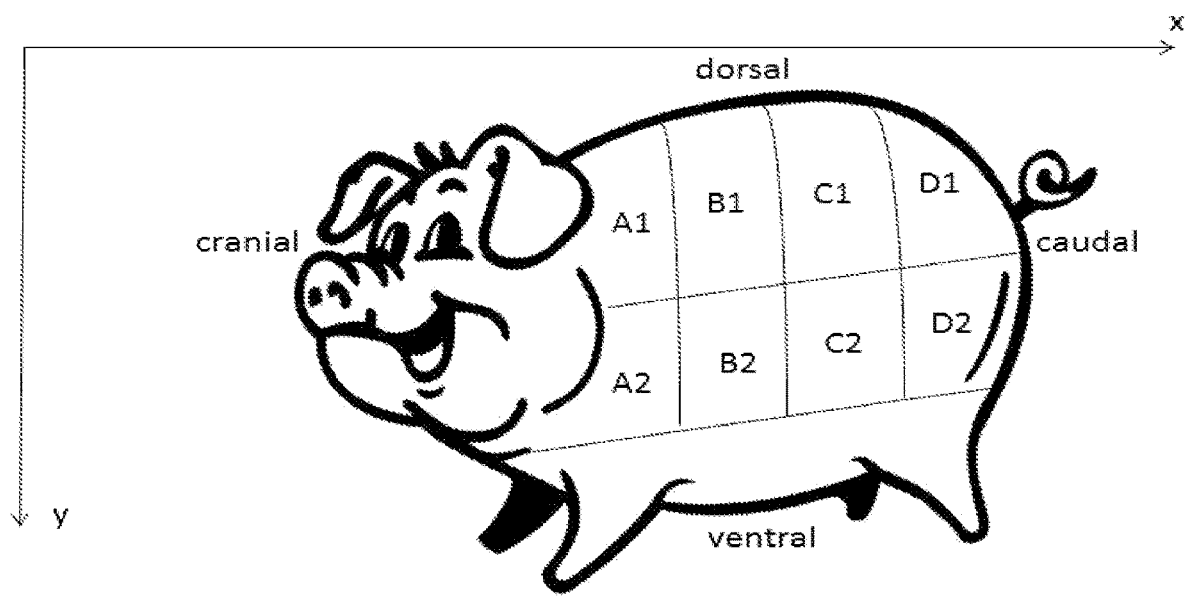
FIG. 1 shows the regions of porcine tissue for evaluation.

The foregoing summary, as well as the following detailed description of certain embodiments of the present application, will be better understood when read in conjunction with the appended drawings. For the purposes of illustration, certain embodiments are shown in the drawings. It should be understood, however, that the claims are not limited to the arrangements and instrumentality shown in the attached drawings. Furthermore, the appearance shown in the drawings is one of many ornamental appearances that can be employed to achieve the stated functions of the system.

DETAILED DESCRIPTION OF THE INVENTION

In one aspect, the present application is directed to the field of biological tissue implants and biological tissue implant processing for transplantation. In a preferred embodiment, the present application is directed to an acellular porcine dermis graft that maintains appropriate mechanical properties, for example, for surgical hernia repair. The terms "graft" and "implant" are used interchangeably herein.

The goal is to sufficiently decellularize porcine dermis to create an acellular graft suitable for human implantation. In porcine dermis samples, this is difficult due to the matrix density and hair follicle depth inherent to this tissue. The process of this application achieves this goal and produces tissue to be used as a graft material for humans. Such tissue must have certain handling characteristics, appropriate histology, and strong biomechanics. The process of this application decellularizes the porcine dermal matrix and maintains sufficient mechanical properties. One procedure where these grafts could be utilized is in human abdominal surgery. Thus, desirable mechanical properties were selected in part from literature review of human abdominal wall biomechanics, where the highest load at failure of the abdominal wall tissue was 10±3.4 N/mm$^2$ and 39N [Hollinsky].

As used herein, the term "passivate" is intended to refer to the elimination of potentially pathogenic organisms and immunogenic substances from an implant. Thus, both sterility and reduced antigenicity is intended by this term, although elimination of beneficial biological properties of the implant, such as osteogenic properties (osteoconduction or osteoinduction; bone fusion), natural tissue functionality, and desirable structural strength of an implant are not intended by this term. The term "passivation" is preferred to the term "sterilize" because, while sterilization is a goal, that term has an absolute connotation for which the ability to definitively test is limited by the state of the art of making such measurements and/or by the need for attendant tissue destruction. In addition, while the implants produced according to the method of this application may not be completely devoid of any antigenicity or pyrogenicity, these undesirable aspects are greatly reduced, and this too is intended by the term "passivation," as used herein. To be suitable for implantation in humans, the grafts (implants) of the present application must be treated to remove, inactivate or substantially reduce any antigenic proteins, which may generate a rejection of the implant. It also must be treated to remove, inactivate or substantially reduce any bacteria and viruses. A desirable treatment process for xenograft dermal tissue also removes or substantially reduces hair and hair follicles.

As used herein, the term "decellularize" is intended to refer to a process that eliminates or sufficiently reduces native cells and cellular material in a tissue such that, when such tissue is implanted, it does not invoke an adverse immune response. The term "acellular" is intended to refer to tissue that is sufficiently reduced in cells and cellular material as to not invoke an adverse immune response.

"Soft tissue", as used herein, refers to any biological tissue other than bone, including but not limited to tendons, ligaments, fascia, whole joints, dura, skin (dermis), pericardia, heart valves, veins, neural tissue, submucosal tissue (e.g. intestinal tissue), and cartilage, or a combination thereof. The "soft tissue" described herein is typically a collagenous material that is autograft, allograft or xenograft, is preferably xenograft and preferably dermis.

"Graft" (or "implant"), as used herein, refers to any material the implantation of which into a human or an animal is considered to be beneficial.

The present application is directed to processes for making a soft tissue implant more suitable for implantation into a recipient, specifically by decellularization of the tissue. Soft tissues (such as dermis) treated according to the present techniques are wholly or partially passivated by contact with cleaning agents, such as solutions containing any of an oxidizing sterilant (for example, hydrogen peroxide), saline, dehydrating agents and/or combinations thereof. The tissues are preferably obtained from xenograft sources for implantation into humans.

The grafts obtained after treatment are biocompatible in human recipients, with no substantively deleterious immune response or rejection due to xenogeneic antigens. The grafts obtained after treatment are in some embodiments bioactive, and achieve healing, remodeling and incorporation in the humans to which they are implanted. These grafts allow for neovascularization and reincorporation with the patient's own tissue. Neovascularization is the proliferation of blood vessels, usually in tissue not normally containing them, and/or of a different kind than usual in a tissue; neovascularization specifically can include formation of functional microvascular networks with red blood cell perfusion. In the context of tissue grafts, neovascularization can include the formation of blood vessels within the tissue graft.

The method of this application provides for implant processing whereby bone marrow, blood, proteins (especially including hair), and particulate matter is efficiently removed, such that what remains is essentially a tissue matrix, passivated tissue matrix, bioinert tissue matrix or bioactive tissue matrix in which a drastic reduction in any form of endogenous material and/or viable organisms is achieved. Creating an acellular matrix is preferred.

In particular, it is noted that the processing methods of the present application related to removal or reduction of antigenic material from tissue may be practiced upon and may be useful for the production of xenografts of multiple tissue types, including soft tissue grafts such as tendons, ligaments, skin (dermis or dermal tissue), dura matter, fascia, and other connective tissues. In some embodiments dermal tissue (skin) is preferred.

The present processes comprise a novel sequence of cleaning agents for treatment of xenograft soft tissue, preferably dermis. In preferred embodiments of the present processes, one or more of the cleaning agents are contacted with the implant comprising the soft tissue to remove blood, fat, cells, proteins, antigens, bacterial, viral, fungal or other material. Cleaning agents include, but are not limited to, detergents, disinfectants (sometimes called disinfecting agents), decontaminants (sometimes called decontaminating agents), antibiotics, virucidal compounds, dehydrating agents and the like. Specialized agents can be used to enhance tissue properties and/or for tissue protection. One, non-limiting, example of a specialized agent are agents to remove hair/hair follicles from dermal tissue. Additionally, solutions that are hypertonic or hypotonic can be used to establish osmotic gradients, for example, by hypo/hyperosmotic soaks.

One embodiment, specifically developed for treating xenograft dermal tissue (e.g. of porcine origin), involves hair removal, hypo/hyperosmotic soaks, hydrogen peroxide, solvent dehydration, and oven drying.

The cleaning agents may be provided in the form of solutions or other mixtures. In some embodiments, the cleaning agent is provided as an aqueous solution (preferably using DI water). Also DI water itself can be used a washing step or in creating osmotic gradients between steps.

For xenograft dermal tissue, the hair and hair follicles should be completely or partially removed to reduce inflammatory responses in vivo. Raw tissue can be partially dehaired by cutting, washing, scrubbing or other means. Further processes for more complete dehairing use chemicals (for example, depilatory substances) to remove animal hair. Various depilatory substances are contemplated, for example, but not limited to thioglycolate or sodium sulfide (NaS). Caustic (basic) solutions are also known to remove hair, along with other agents. Potentially suitable bases can be, but are not limited to, sodium hydroxide (NaOH), potassium hydroxide, lithium hydroxide, $Na_1co$, $Ca(OH)_2$ or $NO_HO$. In some embodiments, the base is NaOH. In some embodiments, the base is used with another depilatory agent, either together or in subsequent steps. Concentrations of less than 5% by weight of NaS are contemplated; in one embodiment, 1% by weight is used. Concentrations of 0.5M or less of NaOH are contemplated; in one embodiment 0.1M NaOH is used. In certain embodiments, NaS and NaOH are used together in a single step. In certain embodiments an alkaline solution containing sodium sulfide having any pH greater than 7 is contemplated, optionally an alkaline solution containing sodium sulfide having any pH greater than 7.5, optionally an alkaline solution containing sodium sulfide having any pH greater than 8, optionally an alkaline solution containing sodium sulfide having any pH greater than 9, optionally an alkaline solution containing sodium sulfide having any pH greater than 10, optionally an alkaline solution containing sodium sulfide having any pH greater than 11, optionally an alkaline solution containing sodium sulfide having any pH greater than 12. In certain embodiments, solutions which have a pH of at least 10 and alternatively at least 12 are preferred.

In some embodiments, an aqueous solution of sodium sulfide is 0.01 to 10 wt-%, alternatively 0.1 to 5 weight-%, alternatively 0.5 to 3 Wt-%, alternatively 0.75 to 1.5 wt-%, and alternatively about 1 wt-% of sodium sulfide.

To adjust the above-mentioned alkaline pH-value, it is provided according to an embodiment of the present invention that an aqueous solution is used which in addition to sodium sulfide contain from 0.001 to 0.5 M sodium hydroxide, alternatively from 0.005 to 0.4 M sodium hydroxide, alternatively from 0.01 to 0.3 M sodium hydroxide, alternatively 0.05 to 0.2 M sodium hydroxide, alternatively, 0.075 to 0.125 M sodium hydroxide, and alternatively from about 0.1 M sodium hydroxide.

Instead of sodium hydroxide, other means for setting the pH values can be used, such as any alkali metal hydroxide or alkaline earth metal hydroxide such as potassium hydroxide, lithium hydroxide, magnesium hydroxide, calcium hydroxide, ammonia and the like.

It is contemplated that the sodium sulfide solution is used in a sufficiently high amount and for a sufficiently long time, so that the dermis is loosened and bristles and hairs are removed almost completely. In some embodiments, the dermis is treated for 1 to 48 hours, alternatively for 5 to 36 hours, alternatively for 12 to 24 hours and alternatively for 14 to 20 hours with an aqueous sodium sulfide containing solution. In a specific embodiment, dermis is treated for 16 hours with an aqueous sodium sulfide containing solution.

Also, the sodium sulfide-containing aqueous solution volume may be 5-fold to 15-fold relative to the volume of the dermis. Alternatively, 6-fold to 14-fold volume, alternatively 7-fold to 13-fold volume, alternatively 8-fold to 12-fold volume, alternatively 9 to 11-fold volume and in certain particular embodiments, approximately 10 times the volume of solution to the volume of the dermis can be used.

In some embodiments, the treatment with the solution containing sodium sulfide, may be carried out one or more times in a row, and the dermis treated with water and/or rinsed between the individual treatment steps with the sodium sulfide-containing solution. In some embodiments only a single treatment of the dermis with the sodium sulfide-containing solution is performed.

Treatment with the sodium sulfide solution or any other treatment steps may be carried out in a rotating drum. Thereby a uniform and complete incubation of the dermis is achieved with the sodium sulfide or other treatments. In some embodiments all treatments are carried out in the same or a similar container, such as a drum. In other embodiments some steps may be carried out in a different container. In some embodiments a container other than a drum may be used.

For example, the rotating drum may be mounted horizontally, and rotate about its axis. Conveniently, on the drum may be provided connections, through which the process solution feeds into the drum and can be removed from the drum. Also on the drum connections may be provided as required to set a higher or lower pressure. Moreover, in some embodiments the drum is designed with double walls, so that the interior cavity of the drum can be heated. Finally, in other embodiments, the drum is designed so that its rotation speed is electronically controlled.

Oxidizing sterilants that may be used in the present processes include peroxides, oxides, hypochlorites, percarboxylic acids, and ozone. A preferred peroxide for use in the present processes is hydrogen peroxide. The oxidizing sterilant may be provided in a solution or mixture, with preferred concentration ranging from about 1% to about 15% percent by weight (weight %). In some embodiments, the concentration of hydrogen peroxide is 3%, other embodiments may use 2%, other embodiments may use 4%.

Additionally an osmotic gradient is used during the process, which generates flow in and out of the tissue. This is also referred to as osmotic cycling (transition from hypotonic to hypertonic solutions). As a non-limiting example, cleaning solutions can be cycled from DI water, to saline and back to DI water.

Saline or salt solutions used in the process include but are not limited to organic and inorganic salt solutions. For reasons such as easy availability and cost, the alkali metal chlorides and alkaline earth metal, in particular sodium chloride, are suitable. Examples of inorganic salts are well known and include, but are not limited to, NaCl, NaF, NaBr, KCl, KF, and KBr. Examples of organic salts include but are not limited to sodium acetate ($CH_3COONa$), potassium citrate ($C_6H_5K_3O_7$), ammonium acetate ($NH_4+CH_3COO-$), sodium lactate ($NaC_3H_5O_3$) or other salts resulting from the reaction product of an organic acid and an inorganic base. For reasons such as easy availability and cost, the alkali metal chlorides and alkaline earth metals, in particular, sodium chloride (NaCl), potassium chloride, lithium chloride, magnesium chloride or calcium chloride can be used. Specific embodiments may utilize sodium chloride (NaCl).

Concentrations of salinity (or salt concentrations) contemplated for use range from about 0.6% to 35%. Specific embodiments may utilize about 26% NaCl, alternatively about 1 to 50 weight-% NaCl, alternatively about 2 to 20 weight-% NaCl, alternatively about 5 to 15 weight-% NaCl. Other specific embodiments use 10% NaCl. Saline (salt) treatments may alternate with water treatments or DI water treatments one or more times in certain embodiments, alternatively four times, alternatively five times, alternatively three times alternating between water and saline to create an osmotic gradient. These saline treatments in some embodiments may last 1 to 48 hours, alternatively 5 to 36 hours, alternatively 12 to 24 hours, alternatively 14 to 20 hours, or about 16 hours.

Solvent dehydration is used in the process, preferably near the end of the process. The tissue is preferably dehydrated with an organic solvent which can be mixed with water. Water contents in the solvent mixture range from about 50% to 0%. Methanol, ethanol, propanol, isopropanol, acetone, methyl ethyl ketone or their mixtures can be used. Specific embodiments may utilize acetone which can be mixed with water. Solvent dehydration is achieved, in some embodiments, with an increasing gradient in solvent, for example starting at a lower concentration and finishing at a higher concentration. In some embodiments, the amount of acetone is about 65-85 percent, which may vary over certain phases of the process. In some embodiments, the water/acetone ratio is 50/50, other embodiments may use 40/60, other embodiments may use 30/70, other embodiments may use 20/80, other embodiments may use 10/90. In some steps, 100% acetone is utilized. This can be conducted in an open or closed bath and racks and trays can be used to hold the tissue, with or without shaking. An acetone gradient allows for gentle water removal. Without a gradient (that is, if tissue is immediately placed in 100% acetone), tissue can be harder and not as flexible. Tolerances for the actual concentrations are wide (65-75% and 85-95%) in the first two steps, then 100% acetone in a final step.

Oven drying is also contemplated, preferably as a last step in the process. Appropriate temperatures are used to allow for complete drying without damage to tissue. In some embodiments, an about 37° C. oven is used; in other embodiments an about 35° C. oven. In some embodiments the oven is a circulating-air drying oven. Tissue is dried until desired dryness level is achieved; in some embodiments, this drying is conducted for about 24 hours, in other embodiments drying is conducted for about 16, 18, 20, 22 hours or more. Racks and trays can be used to hold the tissue. In some embodiments, a convection oven with a laminar flow of 0.2 m/s is used and drying takes place for at least 24 h at 35° C.

In some embodiments all processing of the tissue is conducted at a temperature of no more than about 50° C., alternatively no more than about 45° C., alternatively no more than about 42° C., alternatively no more than about 40° C., alternatively no more than about 38° C., alternatively no more than about 36° C., alternatively no more than about 35° C., alternatively no more than about 34° C., alternatively no more than about 32° C.

The cleaning agents of these processes can be contacted with the implant for a suitable time period in various phases, for example from about 15 min to about 30 min, to about 1 hour, for about 1, 2 or 3 hours, or for longer periods such as about 12 hours, about 16 hours, about 24 hours, about 36 hours or about 48 hours. Phases may be repeated several times, as necessary for complete processing and several steps can be included within one phase (e.g. several rinses included within one phase). The number of phases used depends on the overall process and can include rinsing steps, storing or soaking steps, drying steps, etc. Ten or more phases are contemplated, in some embodiments 15 or more phases are used, in some embodiments 20 or more phases are used, in some embodiments 25 or more phases are used, in some embodiments 26 or more phases are used.

Certain procedures are used in initially providing the dermal tissue for processing. The procedures include, but are not limited to, cleaning the skin of slaughtered pigs with detergent-containing water at a temperature of not more than about 40° C.; removing the skin from the back portion of the pig; removing the bristles from the skin provided above and removal of the subcutaneous tissue and the epidermis from the dermis using a splitting machine.

Detergents to be used for initial cleaning of the skin can be a nonionic detergent, an anionic detergent or both. Nonionic detergents contemplated for use in the process of the application include, but are not limited to, an alcohol ethoxylate, an alkylphenol ethoxylate, an alkyl polyglycoside, a polyoxyethylene ether, a polyoxyethylene sorbitan, or any of the Triton®, Tween® or Brij® series of detergents (e.g. Triton® X-100). Anionic detergents contemplated for use in the process of the application include, but are not limited to, an alkyl benzenesulfonate, an alkyl sulfonate, an alkyl phosphate or an alkyl sulfate, such as the sodium salts of dodecyl sulfate, myristyl sulfate, cetyl sulfate, steryl sulfate and oleyl sulfate (e.g. sodium dodecyl sulfate (SOS; also called SLS)). In some embodiments, sodium dodecyl sulfate (SOS) is preferred.

Specifically in reference to dermal tissue, the tissue is split by mechanical means prior to processing. Only the inferior region of the tissue is utilized for processing, the top of the midsection of the tissue is contemplated. In one embodiment, the raw dermal tissue is recovered from pig (porcine) hide, preferably from specific locations that have improved mechanical properties. The raw tissue is dehaired and defatted by cutting away the undesired portions. The tissue is then pulled through a splitter that has a rotating blade. The tissue is passed through several times until a desired thickness is reached. In some embodiments thicknesses of less than 2 mm or less than about 2.0 mm is desired, preferably 1.5 mm or about 1.5 mm, alternatively 1.0 mm or about 1.0 mm, alternatively less than 1.0 mm or less than about 1.0 mm. Tolerances for thickness are about 0.2 mm. After splitting the tissue is treated with the cleaning agents, as described above.

In certain embodiments, the splitter may have a bandsaw blade. In certain embodiments the splitter may have an endless knife, similar to a bandsaw blade having no teeth. In some embodiments the blade may be mounted horizontally, alternatively vertically, alternatively at an angle to the vertical or to the horizontal which could be 15° or 30° or 45° or 60° or more. In some embodiments the tissue may be delivered to the splitter blade by one or more rollers to be split along the cross sectional area. In certain embodiments, the tolerance for the thickness may be 0.5 mm, alternatively 0.4 mm, alternatively 0.3 mm, alternatively 0.1 mm, alternatively 0.05 mm.

One or more processing steps may be conducted in a mixer or drum which functions to create turbulent flow of the chemicals. Suitable mixers tumble the tissue in a chamber, optionally with baffles to further improve turbulent flow. In one embodiment, a rolling drum mixer is utilized. The filling and emptying of the rolling drum mixer can be conducted with a pump and with venting, and may be made more efficient or more rapid by the use of valves and connectors on the drum, supply lines from the chemical sources, or automated control of chemical flow, filling draining and rolling or mixing. In some embodiments the mixing may be carried out continuously throughout all, most, or some portion of each processing step. In certain embodiments the mixing is continuous throughout the majority of time, alternatively about half the time, alternatively about three-quarters of the time, alternatively about 80% of the time, alternatively about 90% of the time for at least one step, alternatively for two consecutive steps, alternatively for three consecutive steps, alternatively for four or more consecutive steps in the process.

In certain embodiments, the processing may occur in an open or closed vessel. For example, certain aspects of the present application may be carried out in whole or in part within a metal, glass or polymeric beaker or basin with a smooth rim for ease of handling tissues and pouring chemicals into and out of the vessel. Certain aspects of the application may also be practiced using a vessel with a threaded or compression fit lid which screws or snaps on to provide closure to prevent spills or contamination during processing, handling, transport or storage of the tissue.

For xenograft tissue, crosslinking can be used to reduce immunogenicity and strengthen tissue. Chemical agents (such as, for example, glutaraldehyde) used for crosslinking can have deleterious side effects, however. Although crosslinking of the tissue is contemplated, in certain embodiments the tissue is preferably not crosslinked. In certain embodiments, the porcine dermis implant is comprised of non-crosslinked porcine dermis, which acts as a scaffold that allows for neovascularization and reincorporation with a patient's own tissue.

Additionally additional osteoconductive or biologically active materials such as demineralized bone matrix (DBM), mineralized bone matrix, cortical cancellous chips (CCC), crushed cancellous chips, tricalcium phosphate, hydroxyapatite, biphasic calcium phosphate, muscle fibers, collagen fibers, growth factors, antibiotics, cells, or other additives can be utilized in the grafts of the present application. These could be added to the grafts by infusion or used as part of a layered matrix.

After acellular tissue is created through the process of this application as described above, the tissue can be shaped into desired graft configurations. The shaping can be created via punching (also called stamping) or cutting, either by an automated or manual process. Stamping/punching can be performed with a preshaped dye to create desired shapes. Graft shaping can be performed either wet or dry. If grafts are dry, then they can be rehydrated (e.g. with water) before or after shaping. In some embodiments, grafts are dried after processing via solvent dehydration, further dried in an oven, rehydrated with water and then shaped via punching/stamping. Rehydration can be performed in stainless steel or plastic tubs, with or without sealing lids. In some embodiments rehydration is performed for 30 min, in other embodiments rehydration is performed for 45 min, 60 min or more.

Dermis grafts can be provided in several shapes. The shape is predetermined and is based on shapes and sizes most commonly needed for surgeries (e.g. hernia surgery).

Preferred shapes or configurations are a square, rectangle, strip, circle, triangle or oval. Irregular, asymmetric, symmetric, geometric, custom, anatomical, and patterned shapes are also contemplated. For shapes such as rectangles, squares or strips, corners of the grafts can be rounded for ease in use in surgery. Rounded corners (radii) of 20 mm or less are contemplated. In one embodiment the rounded corners (radius) is 15 mm.

In some embodiments, shapes such as squares and rectangles are contemplated. In some embodiments, the grafts have dimensions between about 50 mm and 500 mm. In other embodiments, the grafts have dimensions of about 400 mm, 350 mm, 300 mm, 250 mm, 240 mm, 230 mm, 220 mm, 210 mm, 200 mm, 180 mm, 170 mm, 160 mm, 150 mm, 140 mm, 130 mm, 120 mm, 110 mm, 100 mm, 90 mm, 80 mm, 70 mm, 60 mm, or 50 mm. Tolerances for length and width can be 3%, in some embodiments the tolerance is not less than 5 mm.

Optionally the implants (grafts) are packaged and further sterilized. Packaging can include pouches, bags or other sealable articles. Inner and outer pouches can be used. Grafts can be stored (e.g. at ≤20° C., alternatively at ≤4° C.) before, during or after further sterilization. Further sterilization can include sterilizing with gamma rays (gamma-irradiation) with a minimum dosage of about 15 kilogray (kGy). In other embodiments, irradiation is carried out with a dosage of about 20 kGy.

In certain embodiments, the grafts are stored hydrated and ready-to-use (RTU). Hydration can be performed with biocompatible fluids, for example (but not limited to) water or saline. In some embodiments, the grafts are sealed in a package, and ready-to-use upon removal from the package. Sealing the package using moisture resistant packaging allows for extended storage in a ready to use form. Such packaging allows for the graft to remain in a hydrated form. The grafts can be sealed, for example, in a pouch, and the pouches can be sterilized, such as by low dose gamma irradiation. In certain embodiments, the porcine dermis implant is comprised of non-crosslinked porcine dermis, designed to act as a scaffold that allows for neovascularization and reincorporation with the patient's own tissue.

The present application in some embodiments comprises a soft tissue implant, useful for soft tissue repair procedures such as for hernia repair, designed from xenograft tissue that would take advantage of high tissue availability and animal domestication to be able to control the source tissue material. Xenografts can be porcine, ovine, ratite, equine, caiman, bovine or any other suitable animal source. In certain embodiments the xenografts are preferably porcine.

For grafts to be utilized in hernia repair and other such surgeries, mechanical characterization requirements of load at failure at or above nominally 39N and 10±3.4 N/mm$^2$ were pre-determined based on literature review [Hollinsky]. Unprocessed porcine dermis does not have these required mechanical properties. The goal was to develop a process for treating the xenograft tissue to obtain the required properties so create tissue suitable as a graft for implantation. Testing showed that initial versions of the processed grafts showed variability in biomechanical strength and prompted an investigation into better understanding the variability in relation to the anatomical region of the dermis of the samples.

It was determined that the mechanical properties of porcine dermis vary according to the anatomical location on the hide that the samples are taken from. FIG. 1 shows the anatomical locations studied.

FIG. 1 shows the regions of porcine tissue for evaluation. The porcine dermis was divided into eight pieces and the pieces were labeled by anatomical location using an alpha-numeric identification system. Letter designations from A to D were used to identify the cranial (A) to the caudal (D) regions. A numerical identifier was used for the dorsal (1) to the ventral (2) regions. Mechanical property testing showed that the cranial (region A) and ventral tissues (region 2) showed the weakest biomechanical properties. The B1 and D1 regions showed uni-axial mechanical properties that meet the nominal requirements of load at failure at or above 39 N and 10 N/mm$^2$.

EXAMPLES

Example 1: Processing Porcine Dermis

Porcine dermis samples were processed for evaluation. The process for preparing these samples involves hair removal, hypo/hyperosmotic soaks, hydrogen peroxide, solvent dehydration, and oven drying.

Specific processing of these grafts included storage in 26% NaCl, hair removal with a sodium sulfide/sodium hydroxide ($H_2O_2$) mixture, multiple hypo/hyperosmotic soaks (utilizing NaCl solutions and water), hydrogen peroxide treatment, and then solvent dehydration using acetone, and oven drying at 37° C.

Figure 2A:
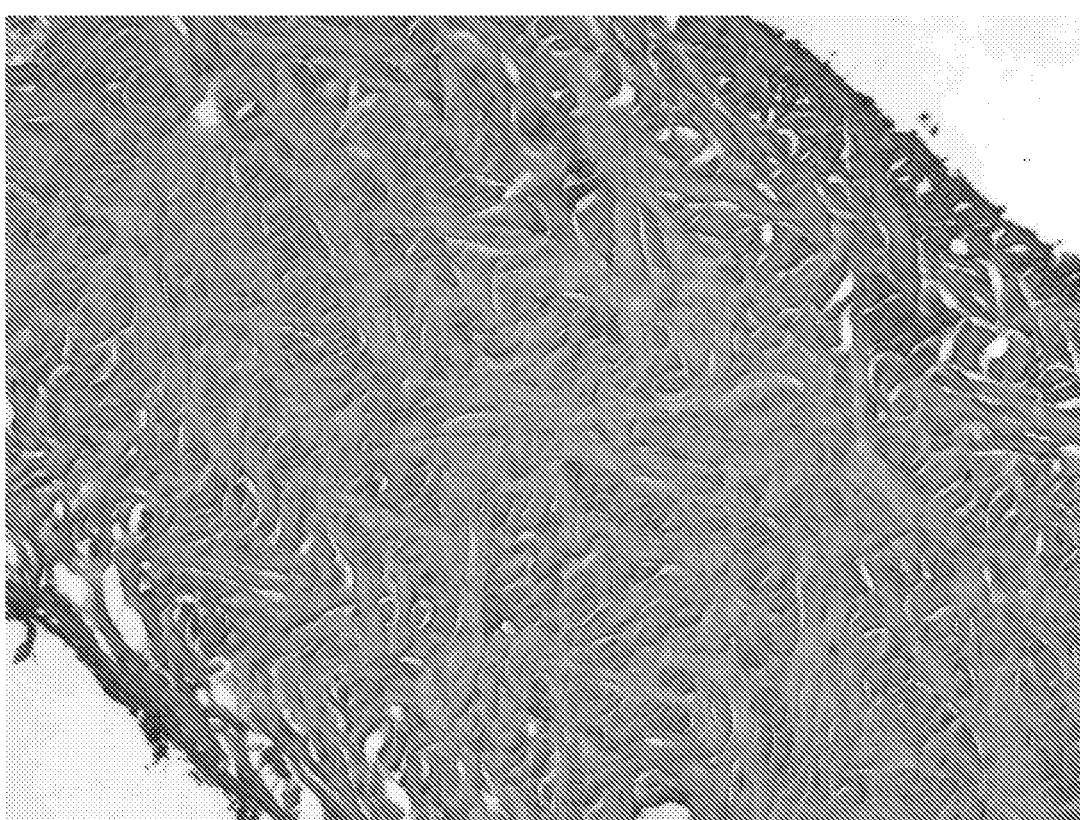
FIGS. 2A and 2B show a histological examination of processed porcine dermal inferior regions.
Figure 2B:
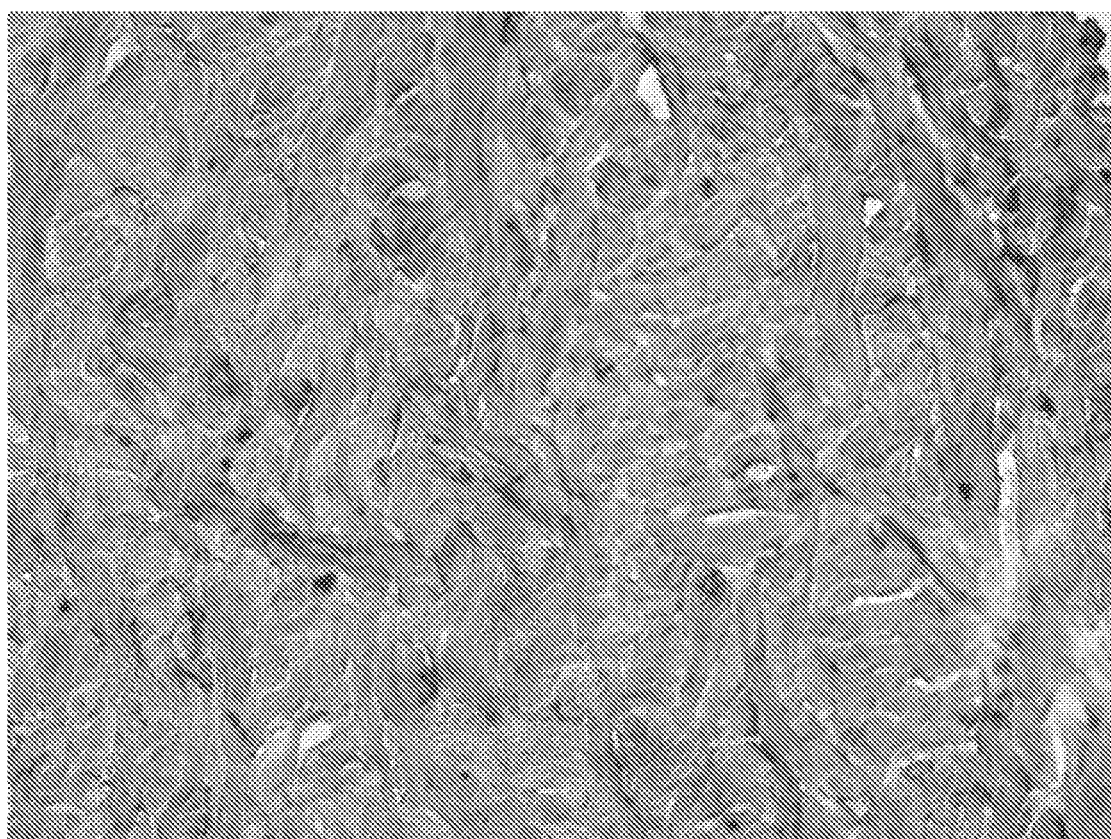

Histological examination of these processed porcine dermal samples was performed, see FIGS. 2A and 2B. FIG. 2A shows H&E stained tissue with 50× magnification and frozen cryostat sectioning. FIG. 2B shows Alcian Blue stained tissue with 100× magnification and frozen cryostat sectioning.

Histological evaluation of the Hematoxylin and eosin (H&E) sections of the processed porcine dermal tissue showed an open porous matrix, see FIG. 2A. This architecture was consistent throughout the tissue. The tissue showed no significant cellular debris, no remnant hair follicles, and no notable adipose throughout the porcine dermal matrix. The histoarchitecture of the native dermal matrix is maintained. The mechanical evaluations of the processed porcine dermis meet the specified requirements of 39N and 10 N/mm$^2$ loads at failure.

Example 2: Processing Porcine Dermis

A freshly slaughtered pig was washed in 40° C. warm water, with 0.1 to 1 wt-% sodium dodecyl sulfate (SOS), for superficial cleaning, before it was skinned. Of the entire skin, the portions of the side of the abdomen were removed and discarded, and only the skin of the back with an area of approximately 800×1200 mm processed.

Then bristles were removed mechanically from the pig skin with a blade before the skin was cut into approximately 400×600 mm sized pieces. After the skin has been introduced with the fat side up into a splitter with two driven wheels and horizontally mounted endless knives with a gap size of 2 mm to separate the excess fat and binder components including the hair roots. Subsequently, the gap dimension of the splitting machine is set to 0.5 mm, and the skin was again passed through the splitting machine to cleave the epidermis, leaving behind a dermis with a thickness of 1.5 mm.

Then the dermis was treated according to the following treatment regimen in a rotating drum:

| Step | Action | Time (hours) |
|---|---|---|
| 1 | Rinse with water (3x) | — |
| 2 | store in water | 0.5 |
| 3 | store in water | 0.5 |
| 4 | treatment with aqueous 1% Sodium sulfide, 0.1M NaOH solution | 16 |
| 5 | Rinse with water (3x) | — |
| 6 | store in water | 1 |
| 7 | store in 10% NaCl | 3 |
| 8 | store in water | 1 |
| 9 | store in 10% NaCl | 16 |
| 10 | Rinse with water (3x) | — |
| 11 | store in water | 1 |
| 12 | store in 10% NaCl | 3 |
| 13 | store in water | 1 |
| 14 | store in 10% NaCl | 16 |
| 15 | Rinsing with water (3x) | — |
| 16 | store in 3% hydrogen peroxide | 24 |
| 17 | store in 3% hydrogen peroxide | 24 |
| 18 | store in 3% hydrogen peroxide | 24 |
| 19 | Rinse with water (3x) | — |
| 20 | store in 70% acetone | 2 |
| 21 | store in 90% acetone | 2 |
| 22 | store in 100% acetone | 2 |
| 23 | store in 100% acetone | 16 |
| 24 | store in 100% acetone | 24 |
| 25 | store in 100% acetone | 24 |
| 26 | drying at 35 [deg.] | 24 |

After the chemical treatment, dermis grafts were punched from the dermis. Grafts were oval in shape and had dimensions of 160×250 mm. These were pairwise welded dry in a laminated plastic film, at 35° C. and gamma-irradiated with a dose of 20 kGy. The thus prepared grafts showed a nearly identical morphology to the native structure.

Example 3: Rat Model Study

Grafts made by a process of the application were studied in a rat model. A sham procedure was used as a control in this study. Sprague-Dawley rats received a unilateral defect, which was repaired with either primary closure or an implanted graft. This study evaluated in vivo cellular infiltration, neovascularization, encapsulation, hematoma/seroma formation, tissue remodeling, and biomechanics at 4- and 8-week sacrifice intervals. This study also evaluated un-implanted graft histology, biomechanics, and tissue degradation properties.

Sprague-Dawley rats were selected based on availability, limited testing expense, and the immune competency of these rats. Sprague-Dawley rats have been used in various other studies with processed soft tissues i.e., human dermis, with positive results. These studies included bilateral defect models and bilateral subcutaneous models. The linea alba defect site was used in the current study to mimic existing literature [1-5].

The decellularization process for the porcine dermis used in this study was performed with $H_2O_2$, osmotic treatment (gradient), Sodium Sulfide and NaOH, and Acetone as in Example 1.

Group I was designated as a control group. Group I rats had a sham procedure performed at the time of surgery, which was repaired by primary closured. Test group rats received a full-thickness abdominal wall defect, which was repaired with a pre-determined acellular porcine dermal matrix [3-5]. Surgical defects were created approximately 0.5 cm lateral to the midline.

The processed porcine dermal samples were prepared for implant the morning of surgery. Sterile technique was used to section all samples for implantation. Samples were sectioned for surgical implant (2×3 cm) in a laminar flow hood. Additional sectioning for mechanical testing, enzymatic degradation, and histology was done non-sterilely. Sterile 50 mL centrifuge tubes used for re-packaging samples sectioned for implantation. Samples were transported to the surgical suite in a poly bag closed with a zip-tie. Samples for time zero evaluation were removed from the hood and tested the day of surgery.

Un-implanted tissue evaluation was performed. Porcine dermis samples were processed, cut-to-size, packaged individually, and terminally sterilized. Samples were shipped at ambient temperatures to the facility, but temperature during shipment was not tracked. All samples were sectioned for implantation and time zero (T=0) testing in a laminar flow hood using aseptic technique the morning of surgery.

Time zero tissue evaluation was performed using histology, tissue thickness measurement, and uni-axial tension testing. This testing was conducted to evaluate tissue cellularity, extracellular matrix properties, degradation properties, and biomechanical properties.

Samples for histological evaluation were sectioned at the time of sample prep for implantation and all extra tissue samples were repackaged and sent for mechanical testing and enzymatic degradation. Samples for histology were immediately submerged in 10% buffered formalin and sent for paraffin embedding and sectioning. Samples were sectioned between 5 and 10 μm thick, mounted on a histology slide, and stained with the appropriate histology staining procedure. Sections were stained with one of the following: H&E, Alcian blue, or Verhoeff Van-Gieson staining. All samples were evaluated after sectioning and staining with a bright field microscope.

Enzymatic degradation assay samples were run in duplicate, with three replications to attain an average of values for each sample. Optical density values were used to calculate mg of degraded collagen per mL of digest solution.

Mechanical testing was performed on an Instron (Model #3366). All uni-axial samples were cut into a dogbone configuration prior to testing. Ball burst samples were cut to 2×2 cm prior to testing. Samples were stored in 0.9% normal saline until mechanical testing. Testing data was used to determine ultimate load at failure and strain.

For surgical implantation, Group I rats, the sham control, received a 2 cm incision lateral to the linea alba (craniocaudal). Two 0.3-0.5 cm transverse incisions, one at the cranial end and one at the caudal end, were created to make a muscle flap. The muscle flap was sutured to the opposing side of the abdominal wall with 5-0 non-resorbable suture using a simple interrupted pattern and ensuring at least 0.3 cm of overlapping tissue.

Rats in the graft implant groups, received a 1×2 cm full-thickness defect lateral to the linea alba. This defect was repaired with a pre-determined implanted matrix. Implants measuring 2×3 cm were used to repair the defect in an overlay fashion. The implants were sutured directly to the abdominal wall, with a minimum of 0.3 cm of overlap between the implant and abdominal wall on each edge of the implant. Implants were sutured with 5-0 non-resorbable suture. All samples were sutured onto the abdominal wall using a simple interrupted pattern; no buckling was present in any of the samples.

At explant, animals were sacrificed at 4 and 8 weeks after surgery. At the time of explant, animals were humanely euthanized. The midline of each animal was opened to access the samples. The samples were excised to include the entire implant or sham repair and a small margin of the abdominal wall. Hematoma/seroma presence was noted at the time of explant.

Each sample was explanted with at least 1 cm of abdominal wall on the edge of each implant for mechanical testing sites. All test explants were photographed with appropriate labeling for identification of test articles. Each explant was measured after excision from the abdominal wall. Explant samples were sectioned to attain two mechanical testing samples and one histology sample. The samples for mechanical testing were sectioned and placed in labeled conical tubes and covered with 0.9% normal saline. Samples were uniaxially tensioned until failure. Samples for histological sectioning were collected with at least 0.5 cm of abdominal wall around the edge of each implant and trimmed to size prior to being submerged into 10% buffered formalin. Samples were sent for sectioning and staining. Samples were embedded in paraffin, sectioned 5 µm thick, and stained with Hematoxylin & Eosin. Evaluation of histopathology data was used for the evaluation of the biological response at 4 and 8 weeks in vivo.

Un-implanted samples of processed porcine dermis measured 1.56 to 1.6 cm throughout the entire material. The pH of the samples was between 6.0 and 6.5 directly out of the package or post-hydration. Histological evaluation of all porcine dermal matrices showed an intact extracellular matrix and no definitive cellular debris.

The protocol utilized for enzymatic degradation is designed to degrade the tissue in vitro over a 24 hour period. The tissue samples are soaked in an enzyme solution at 37° C. for 1, 4, 8, and 24 hours. The solution is filtered to isolate the degraded collagen. The hydroxyproline is then tagged in the solution; this produces various shades of purple indicating concentration of hydroxyproline in the solution. The optical density is measured by an enzyme-linked immunosorbent assay (ELISA) plate reader. The data collected is reported as the collagen degraded in mg per ml of solution. All samples showed a predictable degradation curve over the 24-hour evaluation.

Un-implanted (T=O) samples were evaluated via uniaxial tension testing and ball burst mechanical testing. Uni-axial tension testing data was evaluated with maximum load at failure in Newtons (N) and the load at failure normalized to cross-sectional area (stress) in megapascals (MPa or N/mm2). Porcine dermis grafts had maximum load at failure of $52.04 \pm 19.9$ N and a maximum stress at failure at $6.03 \pm 2.0$ MPa. The grafts also had high burst strengths of $324.59 \pm 62.82$ N.

Animals were explanted at 4 weeks post-operative and showed some residual signs of hematoma/seroma and minor adhesions. Animals used for the sham control showed no signs of adhesions or hematoma/seroma. There was no noted presence of neutrophils, mineralization, necrosis, or encapsulation in any of the samples at the 4-week sacrifice interval. The sham control showed no presence of plasma cells, eosinophils, neutrophils, foreign body reaction, or hematoma/seroma at the 4-week sacrifice interval. The histological evaluation of the 8-week samples showed no indication of the presence of hematoma/seroma, mineralization, necrosis, or encapsulation in any of the samples. There was no foreign body reaction noted in the sham control or in the implants of the current application.

For mechanical testing, the in vivo mechanical samples were sectioned into cranial and caudal portions. The cranial section had a larger portion of intact abdominal wall compared to caudal sections. The dog-bone punch was oriented on each sample to maintain the gauge area centered over the original defect and/or the remaining implanted matrix, while the grip area consisted of abdominal muscle. This ensured the evaluation of the shear properties of the interface strength between the implant the abdominal wall. The porcine dermis grafts exhibited strength at 4 weeks of 7.6N and at 8 weeks of 12.3 N.

There were improvements from 4 to 8 weeks in shear mechanical integrity in all grafts. The grafts had approximately 62% increase in interface strength, and the sham had approximately 40% increase in interface strength from 4 to 8 weeks.

All implanted tissues showed little to no trace of residual cellular debris in the histological sections, which was confirmed by the mild/moderate inflammatory process noted in these samples. There was no noted presence of eosinophils, a cell type indicative of an allergic reaction. The largest differences noted in cell infiltration were the lymphocytes and macrophages. The fibroblast scores increased in all groups from 4 to 8 weeks, which is a naturally occurring process during wound healing. The neovascularization and fibrosis scores were as expected. The implants of the application did not exhibit a foreign body reaction at 8 weeks.

The samples showed acceptable ultimate load and stress at failure and biaxial burst strength. The un-implanted biomechanics, while useful information, are not necessarily indicative of in vivo mechanical properties during the wound healing process. Samples showed a significant increase in shear load from 4 to 8 weeks, which is consistent with the collagen deposition and crosslinking process that occurs after surgical intervention.

The biomechanics and inflammatory responses noted in this study show that the porcine dermis implant samples showed good incorporation, a mild to moderate inflammatory response, neovascularization, no encapsulation, no persistent hematoma, and no persistent foreign body reaction. The biomechanics and biological responses were within acceptable values for dermal meshes. Overall, the results of this study were highly positive indicators that porcine dermis processed using the methods of the present application is rendered sufficiently less immunogenic to prevent acute rejection of the implant.

All patents, test procedures, and other documents cited herein, including priority documents, are fully incorporated by reference to the extent such disclosure is not inconsistent with this application and for all jurisdictions in which such incorporation is permitted.

While the application has been described with reference to certain embodiments, it will be understood by those skilled in the art that various changes may be made and equivalents may be substituted without departing from the scope of the application. In addition, many modifications may be made to adapt a particular situation or material to the teachings of the application without departing from its scope. Therefore, it is intended that the application not be limited to the particular embodiment disclosed, but that the application will include all embodiments falling within the scope of the appended claims.

What is claimed is:

1. A surgical method of using a graft comprising: implanting the graft during surgery, for treatment of a human patient; wherein the graft is prepared by:
    (a) providing a bovine dermis having a native dermal matrix;
    (b) treating the bovine dermis with an aqueous alkaline sodium sulfide solution for at least 1 hour, wherein the aqueous alkaline sodium sulfide solution comprises 0.01% to 1.5% by weight of sodium sulfide and 0.001

M to 0.5 M sodium hydroxide, wherein a pH of the aqueous alkaline sodium sulfide solution is greater than 10;

(c) treating the bovine dermis with a saline solution at least once;

(d) treating the bovine dermis with an aqueous hydrogen peroxide solution at least once;

(e) dehydrating the bovine dermis via solvent dehydration with a solvent starting with a first concentration of the solvent and finishing with a second concentration of the solvent, higher than the first concentration of the solvent; and (f) maintaining a histoarchitecture of the native dermal matrix of the bovine dermis, wherein the graft is non-crosslinked.

2. The surgical method of claim 1, wherein in step (b) the graft is prepared by treating the bovine dermis with the aqueous alkaline sodium sulfide solution for 1 to 48 hours.

3. The surgical method of claim 2, wherein in step (b) a volume in milliliters of the aqueous alkaline sodium sulfide solution is 5 to 15 times a mass of the bovine dermis in grams.

4. The surgical method of claim 1, wherein in step (c) the graft is prepared by treating the bovine dermis two to ten times with the saline solution, wherein the saline solution comprises 1% to 50% by weight of a salt, and wherein the salt comprises an alkali metal or alkaline earth metal and is selected from the group consisting of sodium chloride, potassium chloride, lithium chloride, magnesium chloride, and calcium chloride.

5. The surgical method of claim 1, wherein in step (d) the graft is prepared by treating the bovine dermis two to five times with the aqueous hydrogen peroxide solution, and wherein the aqueous hydrogen peroxide solution comprises 1% to 10% by weight hydrogen peroxide.

6. The surgical method of claim 5, wherein in step (d) the graft is prepared by rinsing the bovine dermis between each treatment with the aqueous hydrogen peroxide solution.

7. The surgical method of claim 1, wherein in step (e) the graft is prepared by dehydrating the bovine dermis two to ten times with the solvent, wherein the solvent is an organic solvent selected from the group consisting of acetone, methanol, ethanol, and isopropyl alcohol.

8. The surgical method of claim 7, wherein in step (e) the graft is prepared by dehydrating the bovine dermis with a first concentration of the solvent of 65-75%.

9. The surgical method of claim 8, wherein in step (e) the graft is prepared by further dehydrating the bovine dermis with a concentration of the solvent of 85-95%.

10. The surgical method of claim 7, wherein in step (e) the graft is prepared by dehydrating the bovine dermis with a second concentration of the solvent of 100%.

11. The surgical method of claim 1, wherein the graft is prepared by rehydrating the bovine dermis after step (e).

12. The surgical method of claim 1, wherein the graft is prepared by punching, stamping, or cutting the bovine dermis into a predetermined shape.

13. The surgical method of claim 12, wherein the graft is prepared by stamping.

14. The surgical method of claim 13, wherein the predetermined shape is a square, rectangle, strip, circle, triangle, oval.

15. The surgical method of claim 13, wherein the predetermined shape is an irregular, asymmetric, symmetric, geometric, custom, anatomical, or patterned shape.

16. The surgical method of claim 12, wherein the predetermined shape is a square, rectangle, strip, circle, triangle, oval.

17. The surgical method of claim 12, wherein the predetermined shape is an irregular, asymmetric, symmetric, geometric, custom, anatomical, or patterned shape.

18. The surgical method of claim 1, wherein the surgery is a hernia surgery, for the treatment of hernia or abdominal repair.

* * * * *